(12) United States Patent
Smoot et al.

(10) Patent No.: US 9,776,097 B2
(45) Date of Patent: Oct. 3, 2017

(54) ARTIFICIAL EYE WITH AN INTERNAL ELECTROMAGNETIC DRIVE

(71) Applicant: DISNEY ENTERPRISES, INC., Burbank, CA (US)

(72) Inventors: Lanny S. Smoot, Thousand Oaks, CA (US); Peter Anastasios Chevako, Los Angeles, CA (US); Eli Joseph Romaire, Los Angeles, CA (US)

(73) Assignee: DISNEY ENTERPRISES, INC., Burbank, CA (US)

( * ) Notice: Subject to any disclaimer, the term of this patent is extended or adjusted under 35 U.S.C. 154(b) by 78 days.

(21) Appl. No.: 14/730,518

(22) Filed: Jun. 4, 2015

(65) Prior Publication Data
US 2016/0354702 A1    Dec. 8, 2016

(51) Int. Cl.
*A63H 33/26*    (2006.01)
*A63H 3/40*    (2006.01)
*A61F 2/14*    (2006.01)

(52) U.S. Cl.
CPC ............... *A63H 3/40* (2013.01); *A61F 2/141* (2013.01)

(58) Field of Classification Search
CPC .................................................. A63H 33/26
USPC ....................................................... 446/131
See application file for complete search history.

(56) References Cited

U.S. PATENT DOCUMENTS

| | | | | |
|---|---|---|---|---|
| 1,309,884 A | * | 7/1919 | Froehlich | A63H 3/40 446/344 |
| 1,686,451 A | * | 10/1928 | Hill | G01R 1/02 324/408 |
| 1,981,333 A | * | 11/1934 | Schavoir | A63H 3/38 446/267 |
| 2,520,491 A | * | 8/1950 | Bunin | A63H 3/40 446/380 |
| 3,423,874 A | * | 1/1969 | Crosman | A63H 3/40 446/132 |
| 3,531,893 A | * | 10/1970 | Samo | A63H 3/40 446/132 |
| 4,208,087 A | * | 6/1980 | Cooper | G02B 27/64 359/557 |
| 5,267,886 A | * | 12/1993 | Wood | A63H 3/006 446/175 |
| 5,900,923 A | * | 5/1999 | Prendergast | G09B 23/28 351/211 |

(Continued)

*Primary Examiner* — Aarti B Berdichevsky
*Assistant Examiner* — Dolores Collins
(74) *Attorney, Agent, or Firm* — Marsh Fischmann & Breyfogle LLP; Kent A. Lembke

(57) ABSTRACT

An artificial eye for use with an animatronic figure or a robot. The artificial eye includes an outer shell formed with a wall defining a spherical inner void space. The outer shell includes a transparent outer or forward portion or half joined with a rear portion or half. The artificial eye includes an inner eye or sphere including a hollow, semi-spherical shell, and the inner eye is positioned in the inner void space of the outer shell. The artificial eye includes an electromagnetic drive positioned within the hollow, semi-spherical shell of the inner eye. The electromagnetic drive supports the inner eye a distance from inner surfaces of the outer shell wall, and the drive includes a pivot joint such as a gimbal operable to pivot the inner eye. The inner eye is supported by a central pivot joint and driven by components centrally located and hidden within the inner eye.

20 Claims, 6 Drawing Sheets

(56) References Cited

U.S. PATENT DOCUMENTS

| | | | |
|---|---|---|---|
| 6,485,142 B1 | 11/2002 | Sheehy et al. | |
| 6,586,859 B2* | 7/2003 | Kornbluh | A63H 13/00 310/309 |
| 6,803,738 B2* | 10/2004 | Erten | H02K 41/031 310/103 |
| 6,879,082 B2* | 4/2005 | Erten | H02K 41/031 310/112 |
| 7,744,442 B2* | 6/2010 | Rettberg | A63H 3/40 446/301 |
| 8,052,502 B2* | 11/2011 | Connolly | A63H 3/006 446/389 |
| 8,337,272 B2* | 12/2012 | Su | A63H 3/38 446/389 |
| 8,512,236 B2* | 8/2013 | Gertner | A61F 9/00821 378/70 |
| 8,715,033 B2* | 5/2014 | Smoot | A61F 2/141 446/131 |
| 8,920,406 B2* | 12/2014 | Gertner | A61F 9/00821 606/11 |
| 2002/0049023 A1 | 4/2002 | Simeray | |
| 2008/0191827 A1 | 8/2008 | Hsiao et al. | |
| 2009/0207239 A1 | 8/2009 | Warmerdam et al. | |
| 2010/0041306 A1 | 2/2010 | Yang | |
| 2014/0114410 A1* | 4/2014 | Breazzano | A61F 2/141 623/4.1 |

* cited by examiner

ARTIFICIAL EYE WITH AN INTERNAL ELECTROMAGNETIC DRIVE

BACKGROUND

1. Field of the Description

The present description relates, in general, to apparatus for simulating a human or human-like eye such as a robotic or animatronic eye or a prosthetic eye (all considered "artificial" eyes), and, more particularly, to an animatronic or prosthetic eye assembly that utilizes fluid-immersion and is electromagnetically driven.

2. Relevant Background

Animatronics is widely used in the entertainment industry to bring mechanized puppets, human and human-like figures, and other characters to life. Animatronics is generally thought of as the use of electronics and robotics to bring inanimate objects alive. Animatronics are used in moviemaking to provide realistic and lifelike action in front of the camera as well as in other entertainment settings such as in theme parks, e.g., to provide lifelike characters in a theme ride or a show. Animatronics are often used in situations where it may be too costly or dangerous for a live actor to provide a performance. Animatronics may be computer controlled or manually controlled with actuation of specific movements obtained with electric motors, pneumatic cylinders, hydraulic cylinders, cable driven mechanisms, and other components that are chosen to suit the particular application including the show or ride setting or stage and the specific character parameters and movement requirements.

In the field of animatronics, there is a continuing demand to provide animatronic characters that better imitate humans and animals. Specifically, much of human and human-like character expression and communication is based on their eyes, including eye contact, eye movement, and gaze direction. With this in mind, designers of robotic and other artificial eyes attempt to mimic the subtle movements and appearance of the human eye to make animatronic figures more lifelike, believable, and engaging. Animatronic designers often have trouble accurately replicating human eye appearance and movement. Challenges arise due to the need for rotation of the eye in a socket in a relatively rapid and smooth manner and also due to the relatively small form factor of the eye in an animatronic figure.

Many types of robotic or animatronic eyes have been created with a number of actuating mechanisms. To actuate or rotate the eye, a drive or actuating mechanism is provided adjacent the eye such as in the animatronic figure's head that includes external motors, hydraulic cylinders, gears, belts, pulleys, and other mechanical drive components to drive or move a spherical or eye-shaped orb. As a result, the eye assemblies require a large amount of external space for their moving parts, and space requirements have become a major issue as the eye itself is often dwarfed by the mechanical equipment used to move the eye up and down (e.g., tilt or pitch) and side-to-side (or yaw). The mechanical drive equipment has moving components external to and attached to the eye that need mounting fixtures and space to freely move. In some cases, existing animatronic eye designs are somewhat unreliable and require significant amounts of maintenance or periodic replacement due, in part, to wear caused by friction of the moving parts including the eye within a socket device. To retrofit an eye assembly, the electromechanical, pneumatic, hydraulic, or other drive or eye-movement systems typically have be completely removed and replaced.

In some cases, animatronic eyes cannot perform at the speeds needed to simulate human eye movement. Movements may also differ from smooth human-like action when the drive has discontinuous or step-like movements, which decreases the realism of the eye. Additionally, many animatronic eye assemblies use a closed loop servo control including a need for a position or other feedback signal such as from optical, magnetic, potentiometer or other position sensing mechanisms. Further, the eye or eyeball's outer surfaces may rub against the seat or socket walls since it is difficult to provide a relatively frictionless support for a rotating sphere or orb, which may further slow its movement, cause wear on painted portions of the eyeball, or even prevent smooth pitch and yaw movements.

More recently, an animatronic eye was created that made use of fluid suspension and an electromagnetic drive, i.e., an eye assembly described in U.S. Pat. No. 8,715,033. The eye assembly includes a spherical, hollow outer shell that contains a suspension liquid. An inner sphere is positioned in the outer shell in the suspension liquid to be centrally floated at a distance away from the shell wall. The inner sphere includes painted portions providing a sclera and iris and includes an unpainted rear portion and front portion or pupil. The shell, liquid, and inner sphere have matching indices of refraction such that interfaces between the components are not readily observed. A drive assembly is provided including permanent magnets on a surface of the inner sphere that are driven by electromagnetic coils located on an external surface of the outer shell.

This animatronic eye's operations were based on having an inner, plastic eye floating (i.e., neutrally buoyant) inside an outer, plastic, fluid-filled, and transparent outer shell. The inner eye or sphere had permanent magnets on its surface that were pulled around by electromagnetic coils on the outer surface of the outer plastic shell. The flotation technique provided extremely low friction, and, because the fluid index matched the inner plastic eye and the outer transparent shell, an illusion was created that the outer surface of the entire eye moved when only the inner eye or sphere actually was rotated.

SUMMARY OF THE INVENTION

While the flotation-based animatronic eye described in the background is relatively compact and is useful for providing frictionless yaw and pitch movements simulating eye movements, the inventors identified several operational issues or challenges with its use. This animatronic eye makes use of external coils in its electromagnetic drive (i.e., used an "external electromagnetic drive" with the drive coils outside the outer shell and the permanent magnets at the surface of the inner sphere or eye), and these coils extended outward, which made them undesirably visible in some applications such as for characters where a large portion of the eye is uncovered (e.g., for an animatronic lizard). Hence, the prior animatronic eye can be considered the externally-driven animatronic eye.

The externally-driven animatronic eye typically was operated such that the inner floating eye or sphere was magnetically-driven in a symmetric manner or it could float off center and, in some cases, drag on the inner surfaces of the outer plastic sphere or shell. This meant the outer drive coils on the outer shell had to be placed symmetrically (e.g., slightly in front of center and behind center) along the east-west equator and north-south meridian. As mentioned above, the coils were then visible in many applications, which often is undesirable as it is desirable to hide the drive components to give the illusion of a natural eye. Additionally, the four magnets provided on the surface of the inner eye or sphere use a small permanent magnet centered between each coil pair on the outer surface of the outer shell as a return spring for the inner eye sphere (return to center when drive forces are removed), and this increased manufacturing complexity and costs.

The externally-driven animatronic eye with its symmetric and external placement of drive coils and driven permanent magnets provides a useful design for some applications. For example, these animatronic eyes can be successfully implemented in certain human animatronic applications where the coils and return spring magnets could readily be hidden or covered by the skin near the front of a human eye. However, other designs may be more desirable including those where a completely open spherical eye is needed (i.e., with no coils being visible). Such applications may include creatures that have eyes that "bulge" outward from their head, e.g., chameleons, such that more than half of the sphere of an eye is visible.

The inventors recognized that there remained a need for improved designs for animatronic or robotic eye assemblies that simulate the appearance and movements of the human eye or an animal's eye. Such designs preferably will have a smaller form factor (or use less space for drive or movement mechanisms) when compared with existing systems, will be designed to be useful in a wider range of applications while still "hiding" the drive components, and be designed to reduce complexities associated with control, manufacture, and/or maintenance.

More particularly, an artificial eye is provided such as may be used in an animatronic figure or a robot or as may be used as a prosthetic eye for a human. The artificial eye includes an outer shell formed with a wall defining a substantially spherical inner void space and having a substantially spherical outer surface. In many applications, the outer shell includes a transparent forward portion joined with a rear portion (e.g., a first shell half (which would provide outer or exterior surfaces and would cover and be proximate to an iris/pupil of an inner eye) and a second shell half (which would be used to mount the shell to a support structure and often not be externally visible)).

The artificial eye may also include an inner eye or sphere comprising a hollow, semi-spherical shell (e.g., a hollow sphere with an opening for receiving drive components), and the inner eye is positioned in the inner void space of the outer shell. The artificial eye also includes an electromagnetic drive positioned within the hollow, semi-spherical shell of the inner eye. In some implementations, the electromagnetic drive supports the inner eye a distance from inner surfaces of the outer shell wall, and the drive includes a pivot joint operable to pivot the inner eye at least in one direction. In this way, the inner eye is supported by a pivot joint that is centrally located within the artificial eye and is driven by components that are also centrally located or at least hidden within the inner eye. The artificial eye may include a volume of liquid ("optical-effect fluid or liquid") contained within the inner void space of the outer shell, and liquid may be selected to transmit light with an index of refraction substantially matching an index of refraction of the forward portion of the outer shell.

In the same or other embodiments, the pivot joint may be or include a gimbal or gimbal-type joint. When a gimbal is used, the electromagnetic drive may include: (a) a sphere-shaped gimbal hub positioned within the hollow, semi-spherical shell of the inner eye; (b) a post or base member extending from the gimbal hub that is affixed at an end to an inner surface of the rear portion of the outer shell; (c) a gimbal bar extending through the gimbal hub and supported upon a gimbal pin; and (d) a gimbal ring coupled with ends of the gimbal bar and with an inner surface of the hollow, semi-spherical shell of the inner eye, with an inner diameter of the gimbal ring being greater than an outer diameter of the gimbal hub (e.g., such that the ring is free to move over the outer surface of the gimbal hub upon the gimbal bar).

In some cases, the electromagnetic drive further may include a plurality of spaced apart permanent magnets on the gimbal ring and a plurality of drive coils mounted on the gimbal hub that are selectively operable to apply drive magnetic fields on the permanent magnets to cause the gimbal ring to move on the pivot joint relative to an outer surface of the gimbal hub. Still further, the electromagnetic drive may include four of the permanent magnets on the gimbal ring and eight of the drive coils on the gimbal hub. Yet further, the electromagnetic drive further may include a restoring permanent magnet positioned on the gimbal hub, e.g., a soft rubber permanent magnet (and the permanent magnets may be selected to "match" their power/strength with that of this restoring magnet).

DETAILED DESCRIPTION OF THE PREFERRED EMBODIMENTS

Figure 1:
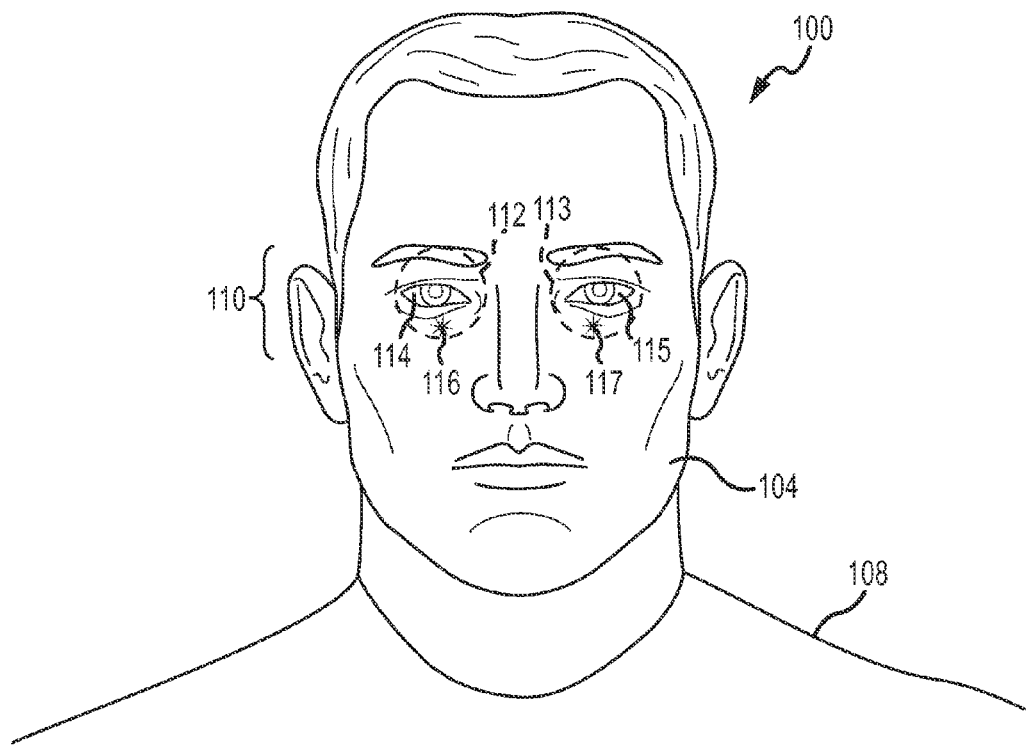
FIG. 1 illustrates a perspective view of an animatronic character or robot including an eye system with a pair of eyes or eye assemblies with internal electromagnetic drives as described herein.

Briefly, embodiments described herein are directed to a compact, fluid-covered (not suspended), electromagnetically-gimbaled (or driven) eye that may be used in eye assemblies for animatronic figures as well as for human prosthetics. Each eye or eye assembly features extremely low operating power, a range of motion and saccade speeds that may exceed that of the human eye while providing an absence of frictional wear points (e.g., between the eyeball or inner sphere and an eye socket). The design of the eye assembly has no external moving parts, which eases its installation in new and retrofit animatronic applications.

The eye assembly (or artificial eye or animatronic/robotic eye) described herein uses a centrally positioned, omnidirectional, pivoting bearing (or pivotal joint or mount) to support the inner eye or sphere. The bearing or pivotal joint can be attached to a post or base member, which, in turn, can be affixed to the outer shell (e.g., the inner half of the outer shell that may be formed of plastic, metal, or other useful material and affixed to the robotic or animatronic head or the like). In this way, the inner sphere or eye does not need to float or be suspended in suspension fluid but may still be contained in or immersed in a fluid to provide a desired appearance or illusion that the entire eye is moving (both the inner sphere and transparent portion or outer half of the outer shell). For example, the outer shell may be filled with an index-matching liquid (matching refractive index of the outer or forward half of the outer shell), but there is no requirement for neutral buoyancy, which significantly widens the choice of the fill liquid.

Because there is no longer a need for a symmetrical magnetic drive as was the case with the fluid-suspension designs, the electromagnetic drive may include coils that drive the inner sphere or eye and can be provided or positioned toward the rear of the eye assembly. Further, because there is no longer a need for a smooth inner surface for the outer shell, some embodiments of the eye assembly can provide these drive coils with a mounting that is wholly within the outer shell such as within the inner sphere or eye itself. Additionally, there is no longer a need for multiple, symmetrically located restoring magnets, and these can be replaced with a single magnet. This single restoring or return magnet can be provided nearly anywhere within the eye assembly such as at the back or rear portion of the inner sphere or eye, and this restoring magnet can act to pull the separate up-down and left-right magnets of the electromagnetic drive toward a neutral position that may be centered vertically and horizontally.

The eye assembly may include a clear or substantially transparent outer shell (or just the outer or forward half may be transparent or translucent) that contains an optical-effect fluid and an inner orb or sphere (e.g., an eyeball). The inner sphere or eye is used to house or contain the electromagnetic drive, and it does not need to be an entire sphere as it typically has an opening to allow the base or post extending from a drive hub to be mounted onto the inner or rearward half of the outer shell. The inner sphere may be a semispherical, hollow, plastic or similar material, shell, which may be painted or colored to provide a desired eye appearance (e.g., white over much of the outer surface, a colored iris, and then a transparent (or dark) pupil). An electromagnetic drive (or drive assembly) is positioned within the inner hollow sphere or inner shell, with a portion affixed to the inner shell to cause the inner shell or eye to rotate or move with that drive portion.

The eye assembly described herein is particularly well suited for applications where a battery is used to power the electromagnetic drive due to its low power requirements and/or consumption. It should be noted that the inventors chose to use a single soft rubber magnet as the return magnet, and it took considerable experimentation to match the disk permanent magnets in the gimble ring to this return magnet. Further, the liquid can be nearly any type of liquid to achieve a desired optical effect such as clear or non-clear, and it may be chosen for its lubricating and/or heat removal qualities such as a glycerin/water mix or silicon oil (e.g., a non-conductive liquid may be useful). The liquid acts as a heat sink as it takes heat away from the coils and distributes it more evenly across the outer shell rather than being concentrated at the coil mount locations. The liquid also acts to provide some dampening of the movement of the gimbal and gimbal ring to avoid "snappy" movements that may be undesirable in some cases.

Figure 2:
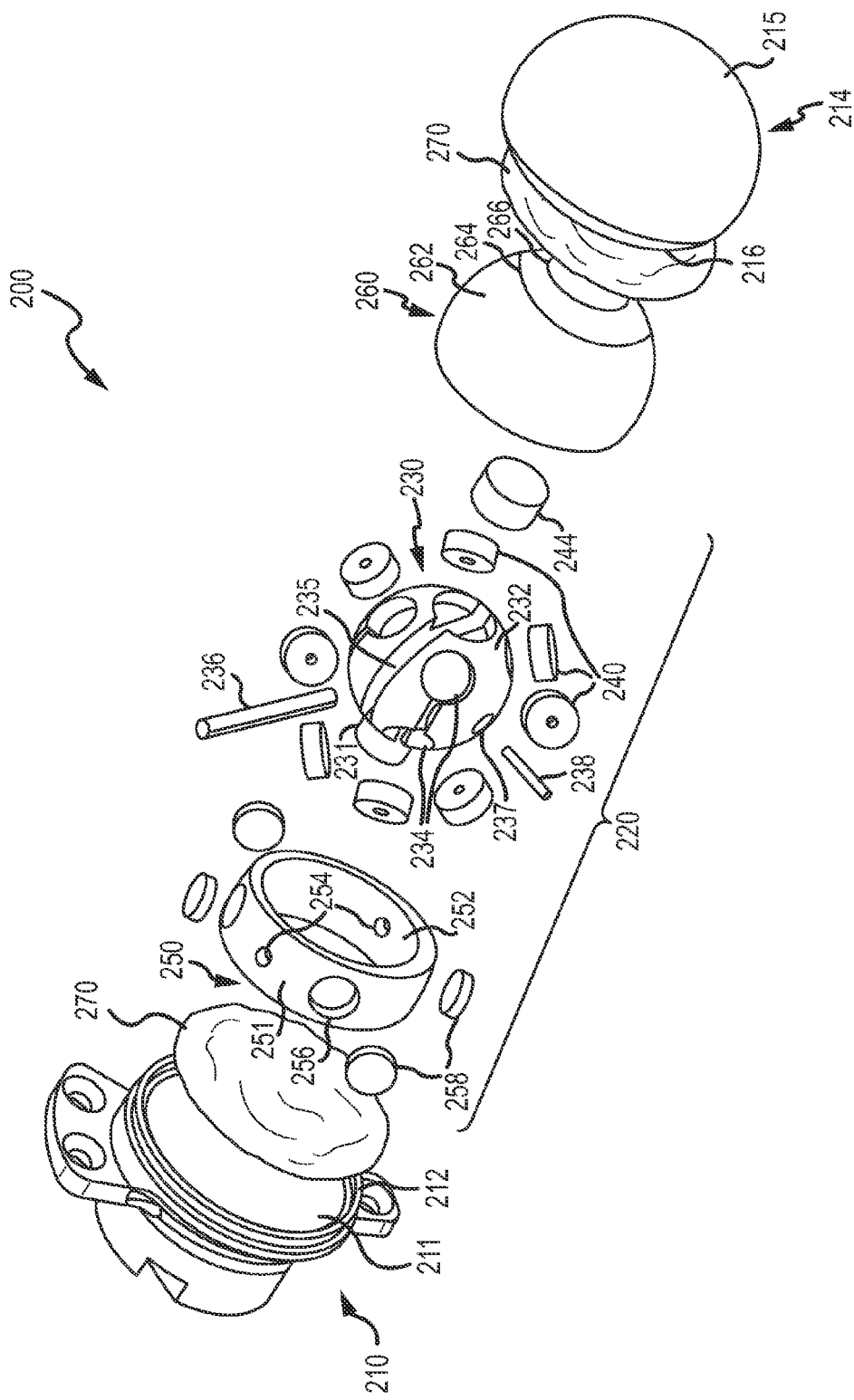
FIG. 2 is an exploded front side view of an animatronic eye assembly as described herein and as may be used in animatronic figures as shown in FIG. 1 or as a prosthetic or artificial eye.

FIG. 1 illustrates an animatronic character or robotic assembly 100 with a head 104 supported upon a body 108 (which is only shown partially for convenience but not as a limitation). Significantly, the animatronic character 100 includes an eye system 110 that may be implemented according to the following description (such as shown in FIG. 2) to provide realistically moving eyes as well as, in some embodiments, an animatronic character 100 with video capabilities. As shown in FIG. 1, the eye system 110 may include first and second eye assemblies 112, 113, and each includes an inner sphere or eyeball 114, 115 that may be driven with internal electromagnetic drive, e.g., through the use of magnetic forces to rotate in any direction as indicated with arrows 116, 117. Here, "internal" means within an outer shell and, more typically, wholly or partially within an inner sphere (or partial sphere) 114, 115 such that no external drive coils or magnets have to be hidden from view with the skin on the head 104 of the animatronic character 100.

The number of eye assemblies 112, 113 is not limiting to this description, with some assemblies 110 including one, two, three, or more eye/eye devices. The eye assemblies may be driven concurrently with the same or differing drive signals (e.g., to rotate similarly or independently) or be driven independently with the same or differing drivers. Two eyes or eye assemblies 112, 113 are shown to indicate that an animatronic character 100 may be provided with stereo video capabilities similar to that of a human by providing a video camera attached in each eye or eye assembly 112, 113 while other embodiments may only include one eye or eye assembly 112, 113 or one camera (e.g., only mount a video camera on an outer shell, for stationary mounting, of one of the two eyes 112, 113).

The specific configuration of the eye assemblies 112, 113 may be varied to practice the animatronic character 100, but FIG. 2 (and other following figures) illustrates one useful eye or eye assembly 200 for providing the animatronic character 100. The exploded view of FIG. 2 is useful for showing that the eye assembly 200 is generally made up of an outer shell provided by a rearward or rear half or portion 210 and a forward half or portion 214 (e.g., the rear portion may be the half or portion of the outer shell that is attached to a robotic or other support and the forward half or portion may be exposed or outer when the assembly 200 is installed (and used to cover the iris/pupil portion of the inner eye)). When assembled, these two outer shell halves (or portions) 210, 214 provide an inner space or volume (e.g., defining a spherical container) for receiving and containing an inner shell or hollow semi or hemisphere (also called inner sphere and inner eye, herein) 260 along with an electromagnetic drive (or drive assembly) 220. The electromagnetic drive 220 can wholly or at least partially be contained within the inner shell 260.

The rear half 210 of the outer shell may be designed to be mounted to the receiving structure for the eye assembly 200. For example, the eye assembly 200 may be provided in a head (or its eye socket) of an animatronic character or robot, and, as shown, the rear portion 210 of the outer shell may include features to allow it to be attached with fasteners to the head or within an eye socket. The rear portion 210 of the outer shell includes a recessed inner surface 211 that may be curved and often is semi-spherical (e.g., for receiving a sphere-shaped object), and the rear portion 210 also includes a lip or engaging surface 212 for contacting and mating with an associated lip or engaging surface 216 of the forward portion 214 of the outer shell, which allows the two halves or portions 210, 214 of the outer shell to be assembled and provide a water-tight seal to allow a volume of an optical-effect liquid 270 to be inserted into and retained in the outer shell formed with rear and forward portions or halves 210, 214.

The rear portion 210 of the outer shell may be formed of plastic or other material and may or may not be transparent to light. The forward portion 214 of the outer shell, in contrast, typically would be formed of a transparent material such that light striking the outer (semi or hemispherical or other shaped) surface 215, and, in some cases, the optical effect liquid 270 will be chosen to match the refractive index of the material used for the forward portion 214 of the outer shell. Note, the forward (and visible, in some cases) portion or "half" 214 of the outer shell may actually be larger than the rear portion or "half" 210 of the outer shell depending upon the intended use of the eye assembly 200 and visibility into the inner portions of the assembly 200 that is desired. As shown and described, the eye assembly 200 includes an outer shell that may be formed of an optically clear or substantially clear material such as a plastic (e.g., a high-grade acrylic or the like), a glass, a ceramic, or the like, and it is hollow with relatively thin outer walls that have an inner surface defining an inner volume or space of the assembly 200. The outer shell may be formed of two or more parts such as a rear and a forward half or hemisphere (elements 210, 214) and may be spherical or nearly spherical in its inner and outer shapes.

The inner shell 260 can be provided in the form of a hollow semi- or hemi-sphere of a material such as plastic or ceramic, e.g., the inner eye 260 may have a hollow, spherical or oblong-shaped body with a large rear opening provided in its outer surface and positioned to face away from the forward portion 214 of the outer shell and toward the rear portion 210 (i.e., to receive the drive 220 or a number of its components/features). It may have an outer surface 262 that can be colored or painted to take the appearance of a natural or fictional eye. For example, the surface 262 may be one color such as white while a central region or ring 264 may be a different color such as to provide an iris. Optically, a central portion 266 may be yet another color or be clear (when a camera, not shown in FIG. 2, is provided) to provide a pupil. The size of the interior volume (e.g., a partial spherical space) defined by the inner shell 260 may vary to practice the eye assembly 200, but is typically chosen to be large enough to receive and mate with the electromagnetic drive assembly 220 (or vice versa). The outer diameter of the inner shell 260 typically is somewhat smaller than an inner diameter of the outer shell and its forward portion or half 214 such that the inner shell or eye 260 can readily move and rotate within the outer shell without contact or rubbing (e.g., at least several mils difference).

The assembly 200 includes an inner sphere or eyeball assembly 260 that is positioned within the outer shell made up of the rear and forward portions 210, 214 and is suspended within a volume of liquid 250 (or suspension liquid or fluid). The eyeball assembly 260 includes a spherical body 262 that may take the form of a hollow ball or sphere formed of an optically clear or substantially transparent material such as a plastic (e.g., a high-grade acrylic or the like), a glass, a ceramic, or the like with outer dimensions that are less than the inner dimensions of the outer shell. In some embodiments of the assembly 200, the spherical body 262 has an outer diameter that is less than the inner diameter of the shell formed of halves/portions 210, 214 by about 20 percent or less such that the body/eye 260 and the outer shell are relatively close fitting with little spacing that is filled with the liquid 270 (e.g., the inner diameter of the outer shell may be 1.5 inches while the outer diameter of the body of inner sphere 260 may be 1.25 inches or more such that a clearance or spacing of about 0.125 inches or less is provided between the body's surfaces and the inner surfaces of the shell with this void or suspension space filled with liquid 270).

The liquid 270 may be chosen to provide desired optical characteristics. The liquid 270 also acts as a "lubricant" for any moving components of the electromagnetic drive, and the liquid 270 further acts as a "coolant" to dissipate and equally distribute/remove heat generated by the drive components (such as its drive coils 240). The optical characteristics may be chosen such that the liquid 270 has an index of refraction that substantially matches that of the outer shell or at least forward portion or half 214 and/or the inner shell/eye 260 such that there is little or no refraction or diffraction at each material/component interface and the shell portion 214, liquid 270, and inner eye 260 may generally act as a single lens or lens assembly (when a camera is included in the assembly 200) and may create an effect where the inner shell/eye 260 appears, to an observer, to be collocated with the outer surface of the forward shell half/portion 214.

Significantly, the eye assembly 200 includes an electromagnetic drive (or drive assembly) 220 that can be partially or wholly contained within the inner shell or sphere 260. This is in contrast to prior artificial eye designs with drive coils on the exterior surface of the outer shell and permanent magnets on the outer surface of the inner eye/sphere. To this end, the electromagnetic drive 220 is affixed or attached rigidly within the eye assembly 200 such as to the outer shell, i.e., to the rear portion/half 210 of the outer shell. Further, the electromagnetic drive 220 is adapted to couple with the inner surfaces of the inner shell/sphere 260 such that it will rotate or move with a driven portion of the electromagnetic drive (in the illustrated example, with the drive or gimbal ring 250).

Still further, the electromagnetic drive 220 is configured to provide a selectively pivotal joint to move the driven portion. This pivotal joint is shown to be a gimbal or gimbal-driven joint, but other pivotal joints that provide movement of the driven portion (e.g., ring 250) in at least one direction could be utilized such as a universal ball joint, a hinge (e.g., for two-directional movement), a bendable strut, a frictionless yoke (e.g., ball and socket), and other well-known or later developed pivotal joints. There is no external mechanical drive, though, with all magnetic components used to move the pivotal joint being provided within the inner shell or sphere 220 so the size of the eye assembly 200 is the outer diameter of the outer shell, and no drive 220 components are visible outside the eye assembly 200.

Turning to the example in FIG. 2, the electromagnetic drive 220 includes a gimbal hub or hub body 230 that is spherical in shape, and a base or post 231 extending outward from one end (e.g., the inner end) that is used to attach or mount the hub 230 to the inner surface 211 of the rear portion/half 210 of the outer shell. In this way, the drive assembly 220 is fixed in place and acts to provide cantilevered support of the inner shell/sphere 260 such that the inner shell/sphere 260 does not need to be supported or float in the optical-effect fluid 270.

The electromagnetic drive 220 includes two to eight or more drive coils 240, and the outer surface 232 of the hub 230 includes a like number of recessed or "receiving" surfaces 234 for receiving the drive coils 240 such that the coils 240 are mounted in the hub 230 are flush with the surface 232. In this example, eight drive coils 240 are used to apply magnetic fields or forces on four driven magnetic elements (e.g., permanent magnets) 258, and the drive coils 240 are equally spaced about the surface 232 such as at about 45 degrees and −45 degrees (e.g., dividing a sphere into eight equal sections and providing a coil 240 centrally in each of these sections on the surface 232 of the hub 230). This provides four pairs of electromagnetic drive coils that can be operated to apply drive forces on magnets 258 to provide desired rotation of the gimbal ring 250 (and coupled inner shell/sphere 260) with pitch and yaw.

When power to the coils 240 is "off," it may be desirable to return the drive 220 and inner shell 260 to a central or "at rest" location. To this end, the drive assembly 220 includes a centering or restoring magnet 244, which is positioned in a recessed surface on the outer surface 232 of the hub 230 such as at a central, front location opposite the post/base 231 (but many other locations may be used). Note, only one restoring magnet 244 is needed to achieve centering of the gimbal ring 250 and inner shell 260 rather than four symmetrically located ones as with prior artificial eyes. The magnet 244 may take many forms to practice the eye assembly 200, but experiments have shown that a soft rubber permanent magnet (e.g., a rubber body with embedded with ferromagnetic particles, a magnet provided by a high-coercivity ferromagnetic compound (such as ferric oxide) mixed with a plastic binder, or other arrangement as used to provide flexible refrigerator-type magnets) is useful for restoring magnetic element 244. This provides a relatively weak magnet with no strong poles, which generates a highly desirable restoring field when it acts on the permanent or driven magnetic elements (e.g., permanent, directional magnets) 258 on the gimbal ring 250.

As discussed above, the pivotal joint of the drive 220 is configured as a gimbal. To this end, the hub 230 includes a slot 235 through which a gimbal bar 236 can pass to extend within the spherical hub/body 230. Additionally, a gimbal or hinge pin 238 is also provided and is inserted through the hole/tunnel 237 in the surface 232 of the hub 230, and the gimbal pin passes through the gimbal bar 236 to provide a gimbal. The ends of the gimbal bar each extend outward a distance from the slot 235.

While the hub 230 is fixed in place in the assembly 200, the inner shell or sphere 260 is affixed or attached to the gimbal ring 250 such that the inner shell 260 moves with the gimbal ring 250. In one embodiment, the gimbal ring 250 is press fit into the inner shell 260 with its exterior surface 251 abutting the inner surface of the shell 260 (e.g., the outer diameter of the ring 250 is substantially equal to or somewhat greater than the inner diameter of a portion of the inner shell 260). The gimbal ring 250 has an inner surface 252 with a diameter that is greater (typically by a small amount) than the outer diameter of the gimbal hub 230 such that the ring 250 can move without friction or contact over the outer surface 232 of the gimbal hub 230 when the electromagnetic drive 220 is operated or the gimbal is used to pivot/rotate the gimbal ring 250.

The gimbal or pivotal joint is completed in the drive 220 by coupling exposed ends of the gimbal bar 236 with mounting holes 254 on the gimbal ring (or ring body) 250. In this way, the ring 250 is gimbal mounted in the drive 220. To drive movement of the gimbal ring 250, the outer surface 251 of the gimbal ring 250 includes four permanent magnet elements 258 in recessed surfaces 256. These are equally spaced apart (e.g., provided every 90 degrees about the circumference of the gimbal ring 250). In one implementation, four directional, permanent magnets were used (e.g., with like poles facing inward toward the hub 230) that were relatively thin (e.g., $\frac{1}{32}$ to $\frac{1}{8}$ inches thick) and small in diameter (e.g., $\frac{1}{16}$ to $\frac{1}{4}$ inches in diameter). Other shapes and sizes may be used, though, to achieve the drive 220 of the present description.

Figure 3:
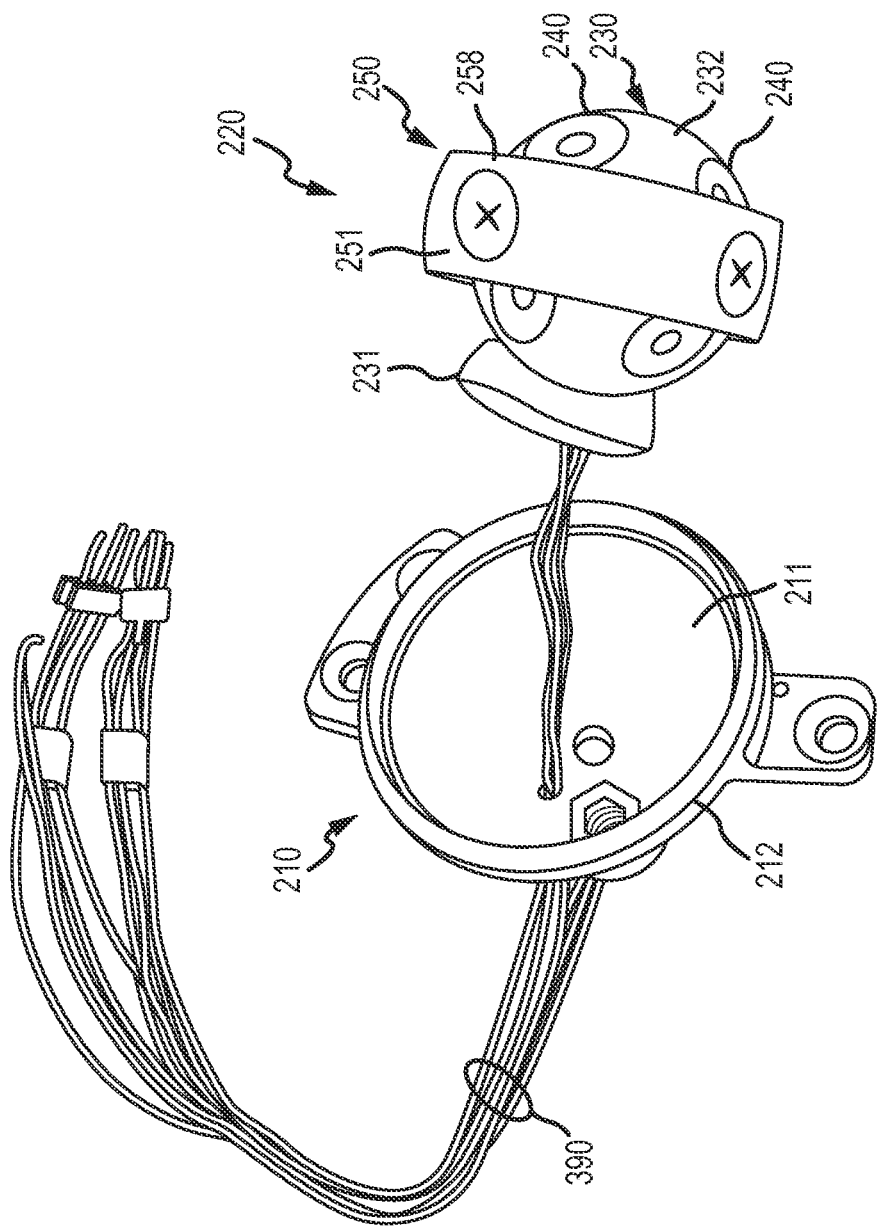
FIG. 3 illustrates a portion of the eye assembly of FIG. 2 with the electromagnetic drive assembled.

Control/driver portions are not shown in FIG. 2 but are described in more detail with reference to FIG. 6. FIG. 3 is provided to show that wires/lines 390 from such controllers/drivers can be run through the inner portion/half of the outer shell (and this hole would be liquid sealed) to the eight drive coils 240. FIG. 3 also shows the electromagnetic drive 220 in its assembled form. Specifically, the gimbal is assembled and the gimbal ring 250 is positioned via the gimbal bar onto the hub 230. The gimbal ring 250 includes the driven magnets 258, with the magnets 258 flush with the ring's outer surface 251. Likewise, the drive coils 240 are mounted onto the exterior surface 232 of the hub 230 so as to be flush or nearly so with surface 232, and the gimbal ring 250 is positioned over the hub 230 with the ring 250 and its directional magnets 258 generally centered between the drive coils 240. The base/post 231 would, upon full assembly of the eye assembly 200, be affixed to the inner surface 211 of the rear portion 210 of the outer shell. The control signals can be used to selectively activate the coils 240 to rotate and move with pitch or tilt/yaw movements of ring 250 and an inner shell later affixed to the ring surface 251.

The magnetic coils 240 can be spaced so as to be adjacent each other but on opposite sides of a great circle (or the equator) of the hub 230. In this way, opposite pairs of the magnetic coils may be thought of as antipodal coils in the drive assembly that may be concurrently operated to drive the ring 250 to rotate through a range of yaw and pitch angles (independently or concurrently to define movement/rotation of the inner shell/sphere 260). For example, axes extending through antipodal pairs of the coils may define a range of motion of about plus or minus 15 to 30 degrees with plus or minus 20 degrees being used in some implementations to define yaw and pitch movement ranges. Specifically, coils 240 may be one pair of antipodal coils that drive the ring 250 and inner shell 260 in the pitch direction while other coils 240 may define the other pitch antipodal coil pair. A set of magnetic elements (e.g., permanent magnets) 258 can correspond in number and position to the drive coils 240 (e.g., 4 permanent magnets may be embedded in the outer surface 251 of the gimbal ring 250 at 90 degree spacings about a great circle or the equator of the ring 250). By concurrently applying equal drive signals to either of (or both of) these antipodal pairs, the eyeball 260 may be caused to pitch or tilt forward or backward by moving the ring 250 on its gimbal mount, and adding driving forces in the yaw drives may be used to cause the eyeball 260 to yaw or move side-to-side to provide a full (or desired amount of movement).

Figure 4:
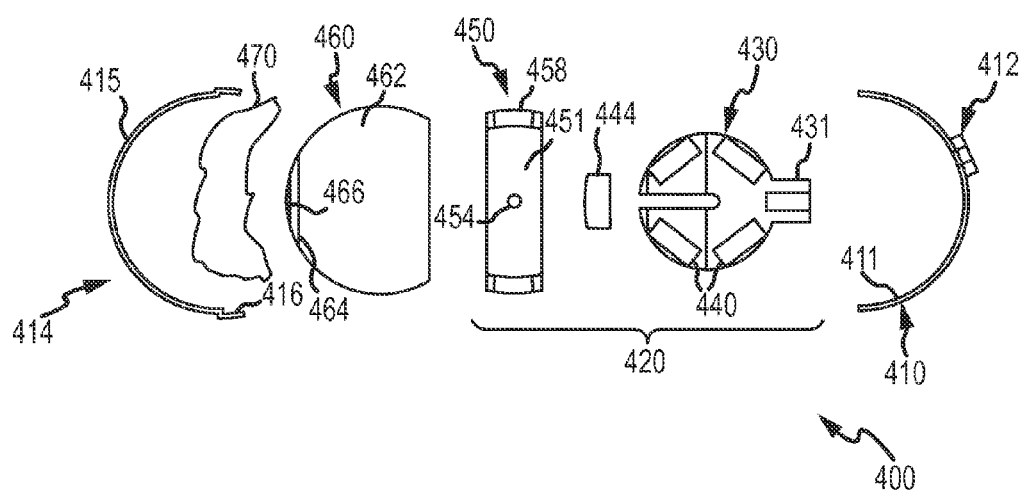
FIG. 4 illustrates an exploded, side view of another eye assembly of the present description.

FIG. 4 illustrates a side, exploded view of another exemplary implementation of an eye assembly 400 similar in configuration as that shown for assembly 200 of FIG. 2. As shown, an outer shell is provided with a rear portion (e.g., a plastic shell) 410 with an inner surface 411 having a hemi or semi-spherical shape, and the rear portion 410 includes a fill port 412 for injecting a volume of an optical-effect fluid or liquid 470. The liquid may have an index of refraction matching that of the outer shell or take another form to achieve a desired effect, e.g., be a colored liquid. The outer shell is further provided with a forward portion or half 414 with a smooth outer surface 415 having a hemi or semi-spherical shape, and the forward portion 414 includes a lip or engagement member 416 for facilitating a water-tight seal with the rear portion 410 of the outer shell (e.g., to define an inner space with a spherical shape in the eye assembly 400).

The eye assembly 400 also includes an electromagnetic drive 420 that, as with drive 220, uses a gimbal as its pivotal joint to support and move an inner shell/sphere 460 (move the inner eye 460). The drive 420 includes a gimbal hub or hub body 430 with a post/base 431 that is affixed or attached to the inner surface 411 of the rear portion 410 of the outer shell so as to rigidly mount the hub 430 in the eye assembly 400. Within the hub 430, the electromagnetic drive 420 includes a plurality of drive coils 440 (e.g., 4 to 8 or the like with 8 typically included in assembly 400). Further, a return or restoring magnet 444 is provided that would be mounted onto or within the outer surface of the hub 430.

The electromagnetic drive 420 also includes a gimbal or drive ring 450 that is slid over the outer surface of the hub 430 and is supported with gimbal bar that would have its ends extend into the ring 450 in gimbal receiving holes 454 in the ring 450. Further, the drive 420 includes one to four or more permanent magnets 458 about the circumference of the ring 450 on the outer surface 451 (but could be provided on the inner surface, in some cases, of the ring 450). In this way, the drive 420 includes a gimbal that allows the ring 450 to be moved with pitch and yaw, for example, with selective operation of the drive coils 440 or pairs of drive coils 440.

Further, the eye assembly 400 includes an inner shell or sphere 460 with an outer surface 462 that may be painted with an iris 464 and pupil 466 in this representative example of the eye assembly 400. The sphere 460 is hollow and has an opening that is large enough to receive the ring 450 and hub 430, and the ring 450 is attached to an inner surface of the inner shell 460 such as by having the outer ring surface 451 mating (e.g., with press fitting) with the shell wall. Hence, when the ring 450 moves with operation of the drive 420 and its coils 440 applying drive forces on the magnets 458, the inner shell or sphere 460 also moves within the liquid 470 in the outer shell. The forward portion 414 and rear portion 410 providing the outer shell of the assembly 400 do not move and neither does the gimbal hub 430.

Figure 5A:
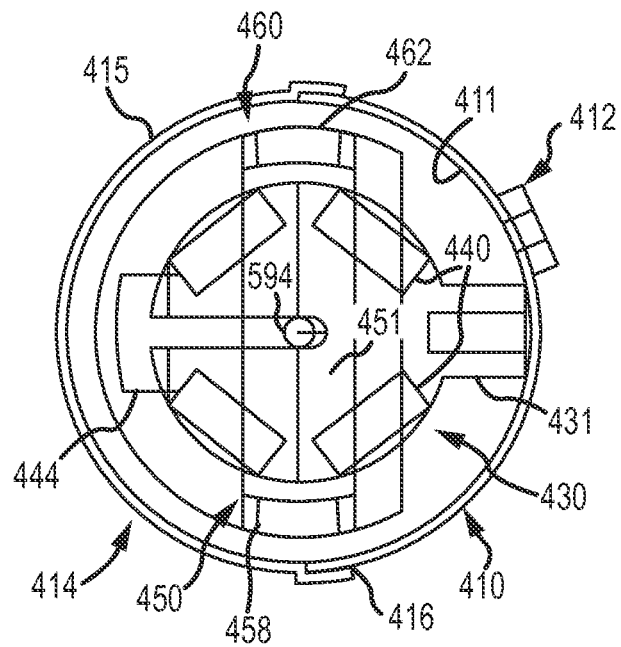
FIGS. 5A and 5B illustrate the eye assembly of FIG. 4 after assembly but with outer components shown to be transparent and other components outlined to show their relative positions.
Figure 5B:
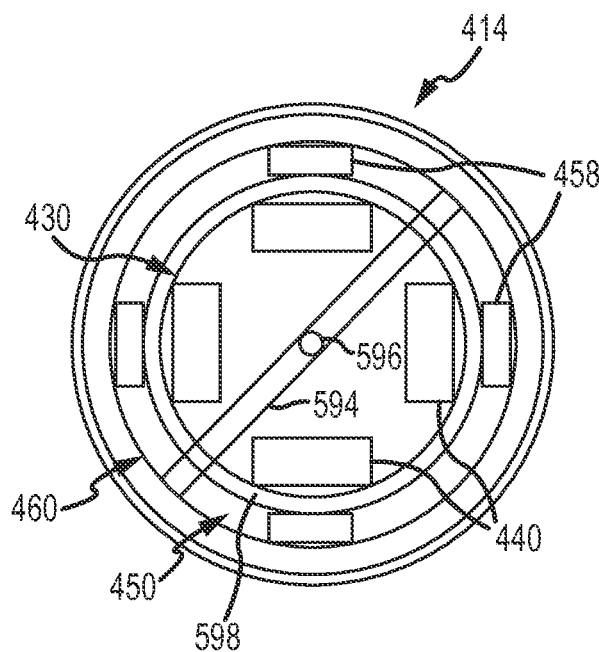

FIGS. 5A and 5B illustrate the eye assembly 400 after assembly and with the outer components shown transparent and inner features outlined to show the relative locations of each component. As shown, the outer shell is provided by the coupling of the rear and forward portions 410 and 414. The hub 430 is affixed to the rear portion 410 via post 431. The gimbal ring 450 is supported by a pivotal joint/gimbal via gimbal bar 594, which has its ends attached to the ring 450, and a gimbal pin 596 coupled with gimbal bar 594. A spacing 598 is provided between the outer surface of the hub 430 and the inner surface of the gimbal ring 450. The inner shell or sphere (or inner eye) 460 is placed over the hub 430 and supported by and attached to the gimbal ring 450 so as to move with the ring 450, which has its movement driven by selective powering of the drive coils 440.

Figure 6:
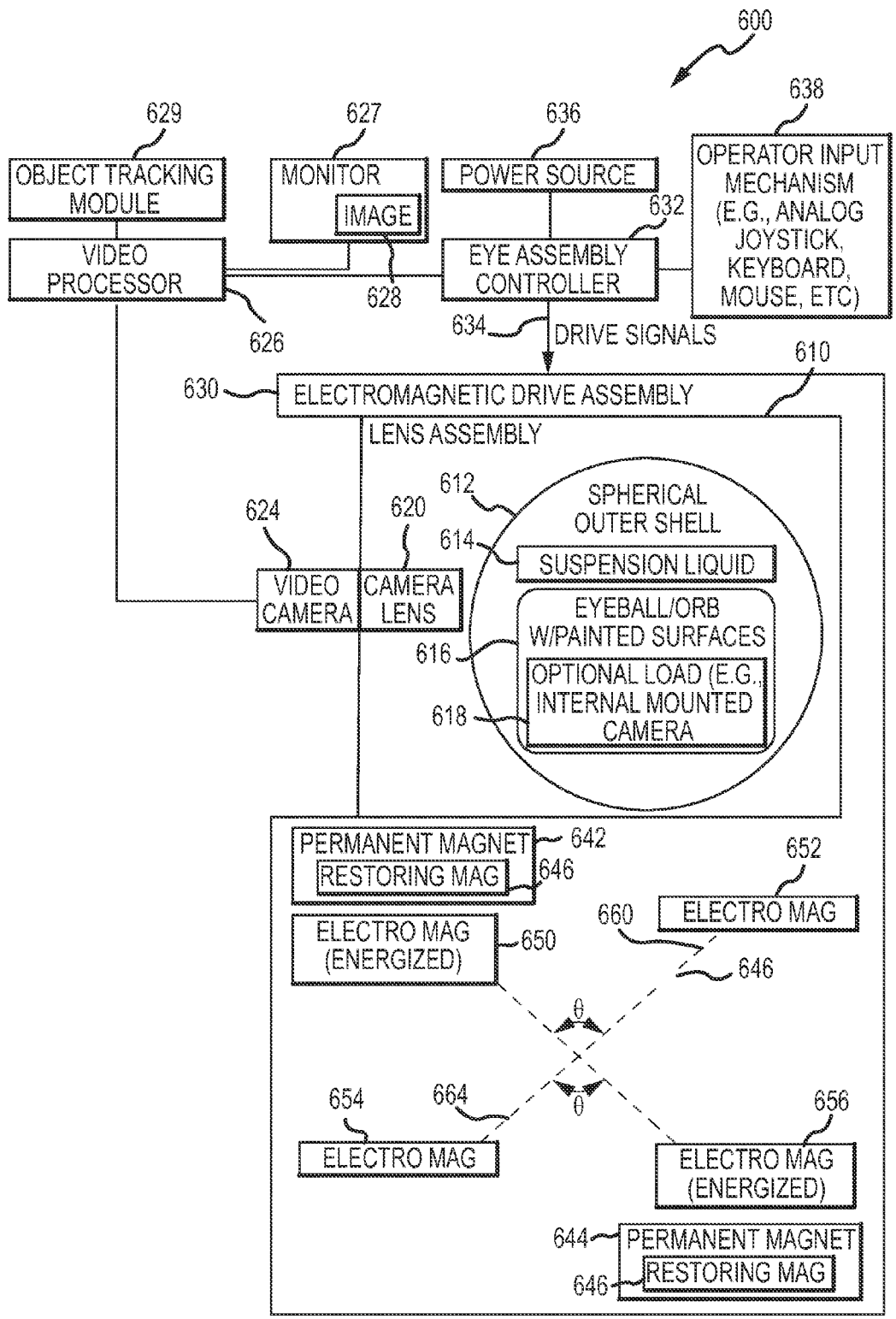
FIG. 6 is a functional block diagram of an animatronic eye assembly such as may be used to implement the assemblies shown in FIGS. 1-5.

FIG. 6 illustrates a functional block diagram of an eye assembly 600 of one embodiment that is useful for showing control (and other) features that may be used to implement the assemblies shown in FIGS. 1-5. The assembly 600 includes a lens assembly 610 that is made up of a spherical outer shell 612 that is typically formed of a transparent or substantially clear thin wall (such as a two part shell of transparent glass, plastic, or the like). An optical-effect liquid 614 is provided within this shell 612 that may have an index of refraction matching or selected based on the index of refraction of the shell 612 as well as to provide coolant characteristics for coils 650-656 (four shown but eight may be provided as shown in other figures).

The lens assembly further includes an eyeball or orb with or without painted surfaces such as a solid sphere of transparent or substantially clear material with an index of refraction matching or selected based on the index of refraction of the liquid 614 (such that interfaces between the orb 616 and liquid 614 are not readily visible to an observer or to the camera 624). The orb 616 may also include an optional load 618 within its interior such as an internally mounted camera in place of or in addition to camera 624 or on an external surface. The lens assembly 610 may also include a camera lens 620 attached to the exterior surface of the shell 612 (such as a hole cut into the shell 612 when a rear portion is opaque or so as to correct/adjust focusing through lens assembly 610). The camera lens 620 may also be provided with or connected to the video camera 624.

The image data from video or other camera 624 are transferred to a video processor 626 for processing such as for display on monitor or display device 627 as shown at 628. The processor 626 may also run an object tracking module 629 to process the image data to determine or recognize an object in the image data and/or track a location of the object relative to the lens assembly 610, and this information may be provided to an eye assembly controller 632 for use in positioning the lens assembly 610 (e.g., to cause the eye assembly 610 to rotate to follow or move a gaze direction based on an object's location or the like).

The assembly 600 uses the eye assembly controller 632 to generate drive signals 634 that are used by the electromagnet drive assembly 630 to rotate/position the lens assembly 610 and, more accurately, to rotate/position the eyeball/orb 616 by moving a drive or gimbal ring within the shell 612 (which is typically stationary and mounted to a frame such as within an animatronic figure) and also within the eyeball/orb 616. A power source 636 may be used by the controller 632 to generate a signal 634 (e.g., a voltage signal or the like) and the operation of controller 632 may follow a saved program (e.g., operate the drive assembly 630 based on code/instructions stored in memory of assembly 600 not shown) and/or based on data from tracking module 629 and/or based on user input mechanism 638 (e.g., a user may input control data via an analogy joystick a keyboard, a mouse, a touchscreen, or other input device).

As shown, the drive assembly 630 includes permanent magnets 642, 644 that are mounted or provided on or in the eyeball or inner sphere 616 on a gimbal or drive ring (not shown in FIG. 6). For example, two, three, four, or more rare earth or other permanent magnets may be embedded or attached to the drive ring that is, in turn, attached to an inner surface of the eyeball or semi-sphere 616 such as a number of magnets equally spaced apart about the surface of the gimbal ring. The drive assembly 630 also includes a restoring magnet 646 that is provided to apply a continuous magnetic field upon the permanent magnets 642, 644 of the drive or gimbal ring to return and maintain the orb 616 at a center or neutral position (e.g., proximate to the magnets 646). Hence, when no (or minimal energy) drive signals 634 are provided, the restoring magnet 646 applies magnetic forces upon the gimbal ring that causes it to return and/or remain in a predefined center or neutral position within the shell 612 (e.g., spaced apart from the shell 612 and with a pupil gazing or directed generally straight outward or another useful position for the application).

The drive assembly 630 provides an electromagnetic-based drive and, to this end, includes a plurality of electromagnets 650, 652, 654, 656 shown (but a larger number typically will be used such as the eight shown in other figures) positioned on or near (close enough to apply adequate magnetic forces on the magnets 642, 644) the outer surface of the gimbal or pivotal joint hub. Typically, sideby-side or paired electromagnets 650, 652 are positioned adjacent to each other but with a center of their coils spaced apart and on opposite hemispheres of the shell 612. In this manner, the restoring magnet 646 may be used to try to retain the magnets 642, 644 in a plane passing through or near a great circle (e.g., equator) of the outer shell 612 while selective energization of antipodal pairs of the electromagnets 650 and 656 or 652, 654 causes the magnets 642, 644 to be displaced from the neutral position.

As shown, axes 660, 664 extend through antipodal points on the spherical shell 612 coinciding generally with centers of coils 650, 656 and 652, 654. The angle, θ, defined by these intersecting axes 660, 664 defines a range of movement of the eyeball 616 relative to a neutral position (e.g., when a plane passes through the restoring magnet 646 as well as the permanent magnets 642, 644), and this range may be plus/minus 15 to 30 degrees such as plus/minus 20 degrees in one embodiment. As shown, the antipodal coils 650, 656 are being energized by the controller 632 with drive signals 634, which as causes a pitch or yaw movement defined by the angle, θ, which may be −20 degrees of pitch or yaw.

In some embodiments, therefore, swiveling the eyeball is achieved with little or no net translational force being applied to the eyeball or inner sphere. A magnet/coil configuration is used that is symmetrical that acts to exert balanced forces around the center of the eyeball or inner sphere so that only (or at least mainly) rotational torques are applied during eyeball/inner sphere pitch and/or yaw (or combinations thereof) movement. In this manner, friction by the eyeball or inner sphere rubbing against the inner surfaces of the outer shell is eliminated because the opposite, equal magnitude driving forces combined with neutral buoyancy provided by the suspension liquid nearly prevent the inner sphere or eyeball from contacting the outer shell during normal operations of the eye assembly.

The controller (such as controller 632) may be a relatively simple design such as an opamp voltage follower circuit used with power source (such as power source 636) to apply a drive voltage (such as signals 634) and, therefore, current to alternating pairs (or antipodal pairs) of the drive coils at the top/bottom and/or left/right sides of the eye assembly. In some cases, a user input device such as an analog joy stick may be used to allow users/operators to quickly move the eyeball or inner sphere by providing and/or modifying the input drive signals via the controller.

One advantage of embodiments of the described eye assemblies is that open loop control may be acceptable for use in all but the most stringent applications because the position of the eyeball or inner sphere may be caused to directly track the strength of the driving magnetic field. Control is simplified, and there is no need for feedback on the eye position. The eyeball or inner sphere may be driven to plus/minus 20 degrees yaw and tilt/pitch such as by approximately plus/minus 200 milliAmps of coil current per axis, and the drive current at the neutral position is 0 milliAmps dues to the no-power restoring magnets. The dynamic drive current can easily be reduced by increasing the number of windings on the drive coils (e.g., if 100 turns of 0.13 mm wire for an approximate 4.5 ohm coil is used, increasing the number of turns likely will reduce the drive current used). Drive coils that wrap completely around the outer shell may be useful in some applications such as to free up more of the front-of-eye view.

While eye assemblies described herein may be particularly well suited for animatronic uses, the eye assemblies may be used in many other settings such as novelties and toys and also for medical or prosthetic applications. This may involve using the above described configurations such as with the drive coils mounted on the outer shell that is used as part of the lens assembly and to contain/hold a volume of liquid and the inner sphere or eyeball. In some prosthetic (or other product/service) applications, though, it may be more useful or desirable to utilize remote coils or other external drive mechanisms spaced apart from the outer shell and further away from the rotated/driven inner sphere.

Although the invention has been described and illustrated with a certain degree of particularity, it is understood that the present disclosure has been made only by way of example, and that numerous changes in the combination and arrangement of parts can be resorted to by those skilled in the art without departing from the spirit and scope of the invention, as hereinafter claimed. As will be appreciated from the above description, the eye assembly provides eyeballs or inner hollow shells/eyes that have a full range of movement (or a range similar to the eye being simulated), and the whole mechanism is hardly bigger than the eyeball itself such that it can be installed in existing animatronic heads without even having to remove the old/existing actuators. The eye assembly has no moving parts outside the outer shell or even outside the inner shell/hollow sphere making it easy for use in retrofitting other eyes or to use in other settings such as a prosthetic or in compact robots, toys, or the like. The drive has low power requirements and consumption making it a useful eye assembly for untethered implementations and use of battery power.

Further, the number of magnetic drives or drive mechanisms and corresponding magnetic elements that are utilized may be varied to practice the eye assemblies described herein. For example, it may be useful to use a number other than 4 such as to use 3 drive mechanisms and 3 corresponding magnetic elements that may be provided at 120-degree intervals along a great circle. In other cases, more than 4 drive mechanisms and magnetic elements may be utilized to suit a particular application.

The improved eye assembly can be considered a large improvement over previous mechanical eyes that used external belts, pulleys, gears, cams, and the like to move an eye. Previous electromagnetic eyes that rely on suspension fluid to support the inner sphere and an external electromagnetic drive had certain usability challenges including limited angular range of movement, visible sight intrusions on the front of the eye assembly due to the drive coils, manufacturing complexity, and inability to easily support "roll-over" eyelids. The eye assembly described herein eliminates, addresses, and overcomes each of these challenges while also providing increased performance and a more deployable package.

More specifically, the visible intrusion of the electromagnetic coils on the surface of the eye assembly has been eliminated, which makes the eye assembly suitable for a vastly enlarged set of character and other uses. The overall new eye assembly can take the shape of a completely smooth sphere simplifying its mounting and requiring no external drive mechanics. Eyelids can now smoothly roll over the new eye shape. The coils of the eye assembly, which generate some heat, are bathed in the index-matching or other optical effect fluid, and this dissipates coil heat throughout the volume of the outer shell so larger currents can be used through smaller diameter wire thus allowing, if desired, a shrinking in the size of the drive coils. The eye assembly can easily have a larger range of rotational movement because the angular spacing of coils at the rear of the eye assembly can be increased without intruding on the front of the eye assembly.

We claim:

1. An artificial eye, comprising:
an outer shell comprising a wall defining a substantially spherical inner void space and having a substantially spherical outer surface, wherein the outer shell includes a transparent forward portion joined with a rear portion;
an inner eyeball comprising a hollow, semi-spherical shell, wherein the hollow, semi-spherical shell is wholly positioned in the inner void space; and
an electromagnetic drive positioned within the hollow, semi-spherical shell of the inner eyeball,
wherein the electromagnetic drive supports the inner eyeball a distance from inner surfaces of the outer shell and includes a pivot joint operable to pivot the inner eyeball at least in one direction,
wherein the pivot joint comprises a gimbal, and
wherein the electromagnetic drive comprises a sphere-shaped gimbal hub wholly positioned within the hollow, semi-spherical shell of the inner eyeball and further comprises a post extending from the gimbal hub that is affixed at an end to an inner surface of the rear portion of the outer shell, whereby the gimbal hub is fixed in position relative to the outer shell and whereby the pivot joint and the gimbal hub of the electromagnetic drive are located within the inner eyeball of the artificial eye.

2. The artificial eye of claim 1, further comprising a volume of liquid contained within the inner void space of the outer shell.

3. The artificial eye of claim 2, wherein the liquid transmits light with an index of refraction substantially matching an index of refraction of the forward portion of the outer shell.

4. The artificial eye of claim 1, wherein the electromagnetic drive further comprises:
a gimbal bar extending through the gimbal hub and supported upon a gimbal pin; and
a gimbal ring coupled with ends of the gimbal bar and with an inner surface of the hollow, semi-spherical shell of the inner eyeball, wherein an inner diameter of the gimbal ring is greater than an outer diameter of the gimbal hub.

5. The artificial eye of claim 4, wherein the electromagnetic drive further comprises a plurality of spaced apart permanent magnets on the gimbal ring and a plurality of drive coils mounted on the gimbal hub that are selectively operable to apply drive magnetic fields on the permanent magnets to cause the gimbal ring to move on the pivot joint relative to an outer surface of the gimbal hub.

6. The artificial eye of claim 5, wherein the electromagnetic drive comprises four of the permanent magnets on the gimbal ring and eight of the drive coils on the gimbal hub.

7. The artificial eye of claim 5, wherein the electromagnetic drive further comprises a restoring permanent magnet positioned on the gimbal hub.

8. The artificial eye of claim 7, wherein the restoring magnet comprises a soft rubber permanent magnet.

9. An animatronic eye for use in an animatronic figure, comprising:
a spherical, hollow outer shell for mounting onto the animatronic figure;
a volume of liquid within the outer shell;
a hollow inner sphere positioned in the liquid and wholly within the outer shell such that an outer surface of the inner sphere is spaced apart from the outer shell; and
a drive assembly comprising a set of magnetic elements wholly positioned within the inner sphere and a set of electromagnetic drive coils also wholly positioned within the inner sphere,
wherein the electromagnetic drive coils are selectively operable to apply magnetic drive forces upon the magnetic elements to rotate the inner sphere about a center point in yaw and pitch directions,
wherein the drive assembly includes a hub,
wherein the hub is positioned within the inner sphere, and
wherein the electromagnetic drive coils are provided on the hub, whereby the set of magnetic elements, the electromagnetic drive coils, and the hub of the drive assembly are located within an interior space of the inner sphere of the animatronic eye.

10. The animatronic eye of claim 9, wherein the hub is rigidly coupled to an inner surface of the outer shell, wherein the drive assembly further includes a drive ring attached to an inner surface of the inner sphere, and wherein the magnetic elements are attached to the drive ring.

11. The animatronic eye of claim 10, wherein the drive assembly includes a gimbal comprising a gimbal bar extending through the hub and connected at each end to the drive ring.

12. The animatronic eye of claim 10, wherein the set of magnetic elements comprise four permanent magnets spaced apart about 90 degrees along an outer surface of the drive ring.

13. The animatronic eye of claim 10, wherein the liquid comprises a liquid with an index of refraction matching an index of refraction of adjacent portions of the outer shell.

14. The animatronic eye of claim 12, wherein the set of drive coils comprises eight, spaced-apart coils on an exterior surface of the hub.

15. An apparatus for use as an artificial eye, comprising:
an outer shell comprising a transparent forward portion joined with a rear portion;
an inner shell with a semi-spherical shape defining an inner void space; and
an electromagnetic drive comprising a hub wholly positioned within the inner void space defined by the inner shell,
wherein the electromagnetic drive supports the inner shell within an interior space of the outer shell at a distance from inner surfaces of the outer shell and includes a pivot joint within the hub allowing movement of the inner shell in at least one direction,
wherein the pivot joint comprises a gimbal,
wherein the electromagnetic drive comprises a post extending from the hub that is attached to the inner surfaces in the rear portion of the outer shell such that the hub is rigidly coupled to the outer shell,
wherein, except for the post, the electromagnetic drive is enclosed within the inner shell, and
wherein the inner shell has an outer surface free of any components of the electromagnetic drive.

16. The apparatus of claim 15, wherein the electromagnetic drive further comprises:
a gimbal bar extending through the hub and supported upon a gimbal pin; and
a gimbal ring coupled with ends of the gimbal bar and with an inner surface of the inner shell.

17. The apparatus of claim 16, wherein the electromagnetic drive further comprises at least one permanent magnet on the gimbal ring and at least two drive coils mounted on the gimbal hub that are selectively operable to apply drive magnetic fields on the at least one permanent magnet to cause the gimbal ring to move on the pivot joint relative to an outer surface of the gimbal hub.

18. The apparatus of claim 17, wherein the electromagnetic drive comprises four of the permanent magnets on the gimbal ring and eight of the drive coils on the gimbal hub.

19. The apparatus of claim 17 wherein the electromagnetic drive further comprises a restoring magnetic element positioned on the gimbal hub.

20. The apparatus of claim 19, wherein the restoring magnetic element comprises a soft rubber permanent magnet.

\* \* \* \* \*